(12) United States Patent
Andersen et al.

(10) Patent No.: US 10,231,814 B2
(45) Date of Patent: Mar. 19, 2019

(54) VENA CAVA FILTER

(71) Applicant: COOK MEDICAL TECHNOLOGIES LLC, Bloomington, IN (US)

(72) Inventors: Torben Peter Andersen, Taastrup (DK); Jens Kold, Ringstead (DK)

(73) Assignee: COOK MEDICAL TECHNOLOGIES LLC, Bloomingon, IN (US)

( * ) Notice: Subject to any disclaimer, the term of this patent is extended or adjusted under 35 U.S.C. 154(b) by 847 days.

(21) Appl. No.: 14/480,930

(22) Filed: Sep. 9, 2014

(65) Prior Publication Data
US 2015/0073470 A1    Mar. 12, 2015

(30) Foreign Application Priority Data

Sep. 9, 2013  (GB) .................................. 1316019.7

(51) Int. Cl.
*A61F 2/01* (2006.01)
*A61B 17/12* (2006.01)

(52) U.S. Cl.
CPC .......... *A61F 2/01* (2013.01); *A61B 17/12109* (2013.01); *A61F 2002/016* (2013.01);
(Continued)

(58) Field of Classification Search
CPC .......... A61F 2002/016; A61F 2/01–2002/018; A61B 17/12036; A61B 17/12109; A61B 17/1214–17/12154
(Continued)

(56) References Cited

U.S. PATENT DOCUMENTS

| 4,807,626 A | * | 2/1989 | McGirr | ................ A61B 17/221 |
| | | | | 600/436 |
| 5,133,733 A | * | 7/1992 | Rasmussen | ............... A61F 2/01 |
| | | | | 606/200 |

(Continued)

FOREIGN PATENT DOCUMENTS

| DE | 29500864 U1 | 5/1996 |
| EP | 2604222 A1 | 12/2011 |

(Continued)

OTHER PUBLICATIONS

Extended European Search Report EP 14275184.1-1651 (dated Jan. 29, 2015).

*Primary Examiner* — Ryan J Severson
*Assistant Examiner* — Charles Wei
(74) *Attorney, Agent, or Firm* — Brinks Gilson & Lione

(57) ABSTRACT

The disclosure provides an implantable medical device comprising a material capture element, which has a generally closed conical deployed shape and a narrow end disposed at or proximate the first end of the device. The material capture element includes a wide end facing the second end of the device, the material capture element having a zone of wider radial dimension which provides a first vessel contact site. A plurality of wire tethers are coupled to the wide end and extend to the second end. The wire tethers define a substantially open passageway for blood and provide a second vessel contact site. The first and second contact sites are spaced longitudinally from one another to provide stability. A first retrieval element is disposed at the first end and coupled to the narrow end, while a second retrieval element is disposed at the second end and coupled to the wire tethers.

18 Claims, 3 Drawing Sheets

(52) U.S. Cl.
CPC ............... *A61F 2230/0078* (2013.01); *A61F 2250/0039* (2013.01)

(58) Field of Classification Search
USPC .......................................... 606/200
See application file for complete search history.

(56) References Cited

U.S. PATENT DOCUMENTS

| | | | | |
|---|---|---|---|---|
| 7,763,044 | B2* | 7/2010 | Inoue | A61F 2/01 606/200 |
| 7,803,171 | B1* | 9/2010 | Uflacker | A61F 2/01 606/200 |
| 2002/0143360 | A1* | 10/2002 | Douk | A61B 17/12022 606/200 |
| 2002/0193828 | A1* | 12/2002 | Griffin | A61F 2/01 606/200 |
| 2003/0065354 | A1 | 4/2003 | Boyle et al. | |
| 2005/0096692 | A1* | 5/2005 | Linder | A61F 2/013 606/200 |
| 2005/0131452 | A1 | 6/2005 | Walak et al. | |
| 2006/0079928 | A1 | 4/2006 | Cartier et al. | |
| 2007/0066991 | A1 | 3/2007 | Magnuson | |
| 2007/0078481 | A1 | 4/2007 | Magnuson et al. | |
| 2009/0299403 | A1* | 12/2009 | Chanduszko | A61F 2/01 606/200 |
| 2010/0030254 | A1 | 2/2010 | Chanduszko et al. | |
| 2010/0211094 | A1 | 8/2010 | Sargent, Jr. | |
| 2010/0274277 | A1 | 10/2010 | Eaton | |
| 2012/0071914 | A1 | 3/2012 | Shrivastava | |
| 2013/0006295 | A1* | 1/2013 | Chanduszko | A61F 2/01 606/200 |
| 2013/0158591 | A1* | 6/2013 | Koehler | A61F 2/01 606/200 |
| 2013/0226224 | A1* | 8/2013 | Snow | A61F 2/01 606/200 |

FOREIGN PATENT DOCUMENTS

| | | |
|---|---|---|
| WO | WO 1995/13761 | 5/1995 |
| WO | WO 2002/102280 A2 | 12/2002 |
| WO | WO 2003/002032 A2 | 1/2003 |
| WO | WO 2006/074163 A2 | 7/2006 |

* cited by examiner

VENA CAVA FILTER

CROSS-REFERENCE TO RELATED APPLICATIONS

This application claims the benefit of priority under 35 U.S.C. § 119(a) to G.B. Patent Application Number 1316019.7, filed Sep. 9, 2013, which is incorporated by reference here in its entirety.

TECHNICAL FIELD

The present invention relates primarily to a vena cava filter although the structure of device taught herein can equally be used for an occlusion device. The skilled person will also appreciate that the device could be used in other parts of a patient's anatomy and not just in the vena cava.

BACKGROUND ART

Filters for placement in the vena cava are well known. A preferred filter shape is conical and sized such that the wide end of the cone is sufficiently large to be able to abut and press against the vessel wall, often fixed thereto by barbs or similar anchoring devices. The narrow end of the filter is typically closed. The filter is often formed as a mesh of wires or struts having apertures which are sufficiently large to allow fluid therethrough but small enough to trap debris and thrombus material. A conical shape has the advantage that the cone tends to expand as a result of blood flow pressing into the filter, which thereby assists in holding the filter in place.

A problem with such filter designs is that there is a risk of deploying the filter at an angle in the vessel, that is with the open end of the cone not properly aligned in the plane transverse to the vessel. Even if it is deployed accurately, there is the risk that the filter tilts over time. Any such tilt of the filter can result in loss of patency, or sealing, to the vessel wall and as a result loss of filtration function. Tilting can also cause loss of coupling to the vessel wall, which can result in migration of the filter over time. The art has sought to address these problems by modification of the delivery assembly, for instance to provide devices which seek to position the narrow end of the filter at the centre point of the vessel. Alternatively or additionally, the generally conical filter design may be modified by the addition of stabilising struts and the like, for instance by providing a double filter structure with opposing filter cones.

While a specially designed deployment assembly may reduce or substantially avoid the risk of incorrect placement of the filter in a vessel, it has no further function after deployment and as a result cannot assist in maintaining proper orientation of the filter after deployment.

The addition of further stabilising struts to a conical filter can add bulk to the structure, particularly when the filter is radially compressed for deployment purposes. Furthermore, known stabilising structures are such that they are liable to impinge on fluid flow, thereby risking the generation of thrombi. This can be particularly the case with double cone symmetrical filter designs.

Moreover, vena cava and other filters tend to be temporary medical devices requiring removal once the period of treatment has been completed. A problem with conical shaped filters lies in the lack of options with regard to retrieval, in that they normally must be retrieved from their narrow or closed end first. In addition, conical shaped filters tend to be harder to reposition once deployed in the patient's vessel.

The skilled person will appreciate that at least some of the above considerations can apply equally to occlusion devices of conical form.

Examples of filters can be found in WO-2006/074163, US-2012/0071914, WO-02/102280, US-2010/0030254, WO-95/13761 and German Utility Model DE-29/500,864U. Examples of embolic protection devices can be found in US-2010/0274277, US-2007/0066991, US-2007/0078481 and US-2010/0211094.

BRIEF SUMMARY

The present invention seeks to provide an improved implantable medical device and, in the preferred embodiments, an improved vena cava filter. It will be appreciated though that the teachings herein can be applied to filters for placement in other body vessels and also to occlusion devices. The teachings herein can also be applied to embolic protection devices.

According to an aspect of the present invention, there is provided an implantable medical device having first and second ends and a longitudinal dimension, the device including: a material capture element having a generally closed conical deployed shape with a narrow end disposed at or proximate the first end of the device, and a wide end facing the second end of the device; the material capture element having a zone of wider radial dimension providing a first vessel contact site of the device; a plurality of wire tethers coupled to the capture element at the wide end thereof, the wire tethers extending to the second end of the device and defining a substantially open passageway for blood and particulate material therethrough; the wire tethers having portions of wider radial dimension providing a second vessel contact site of the device, the first and second contact sites being spaced from one another in the longitudinal dimension of the device; a first retrieval element disposed at the first end of the device and coupled to the narrow end of the capture element; and a second retrieval element disposed at the second end of the device and coupled to the wire tethers.

This structure provides a number of advantages. The wire tethers provide a second retrieval point for the medical device, which means that it can be retrieved from either end once implanted in a vessel. The two retrieval points also provide a structure which enables repositioning of the device after deployment.

The shapes of the conical portion and of the wire tethers provide two longitudinally spaced contact sites along the length of the device, which give the device orientational stability in the vessel and minimizes the risk of tilting of the device.

Furthermore, the wire tethers do not impinge upon or disturb blood flow, thereby minimizing the risk of thrombus formation at the tethers.

In an embodiment, the capture element includes a frame having a plurality of frame elements extending to the open end of the capture element; the wire tethers being coupled to respective ones of the frame elements at the open end of the capture element.

Preferably, the capture element provides a substantially closed conical capture basket.

Advantageously, the wire tethers have a curved deployed shape providing the portions of wider radial dimension. Such a shape can reduce the risk of vessel damage or trauma.

In an embodiment, the wide end of the capture element has a taper, which taper provides the zone of wider radial dimension and first vessel contact site.

It is preferred that the first and second contact sites each include circumferentially spaced contact elements.

It is not excluded that the device could be provided with more than two contact sites along the length of the device, the contact sites being spaced form one another.

Advantageously, the wire tethers taper to the second end of the device.

In the preferred embodiments, the first and second retrieval elements face opposing directions. The first and second retrieval elements may include a retrieval hook or catch.

Preferably, the device is a filter, in particular a vena cava filter.

According to another aspect of the present invention, there is provided a method of deploying an implantable medical device, the device having first and second ends and including a material capture element having a generally closed conical deployed shape with a narrow end disposed at or proximate the first end of the device, and a wide end facing the second end of the device; the material capture element having a zone of wider radial dimension providing a first vessel contact site of the device; a plurality of wire tethers coupled to the capture element at the wide end thereof, the wire tethers extending to the second end of the device and defining a substantially open passageway for blood and particulate material therethrough; the wire tethers having portions of wider radial dimension providing a second vessel contact site of the device, the first and second contact sites being spaced from one another in the longitudinal dimension of the device; a first retrieval element disposed at the first end of the device and coupled to the narrow end of the capture element; and a second retrieval element disposed at the second end of the device and coupled to the wire tethers; the method including the steps of:

inserting the device endoluminally in a patient in a radially contracted configuration; providing for expansion of the device in a vessel of the patient with the second end of the device in a downstream blood flow position relative to the second end of the device such that the capture element is disposed with the open end thereof facing upstream; whereby the first and second contact sites maintain orientation of the device in the vessel.

The method may include the step of subsequently retrieving the medical device from the patient by coupling a retrieval apparatus to the second retrieval element from an upstream direction of the vessel, the retrieval apparatus including a sheath sized to receive the medical device, the wire tethers acting to pull and radially compress the capture element into the sheath.

Other features and advantages will become apparent from the following detailed description of the preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There is described below a preferred embodiment of the present invention, which is configured as a vena cava filter. It is to be understood though that the teachings herein are not limited to vena cava filters and are equally applicable to filters disposed in other body lumens and can also be modified to form an occlusion device or an embolic protection device.

Figure 1:
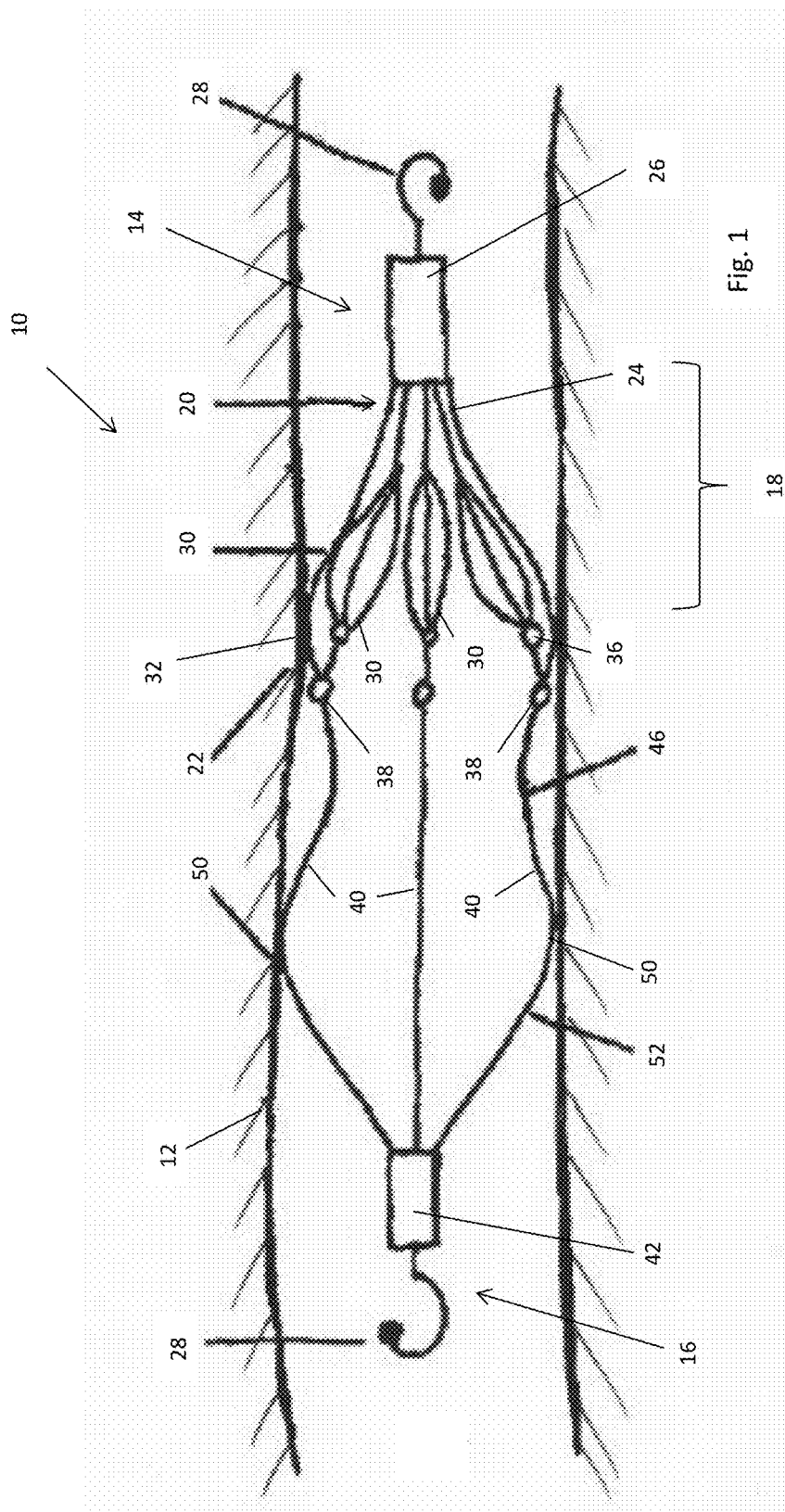
FIG. 1 shows in schematic form a preferred embodiment of vena cava filter deployed in a patient.

Referring first to FIG. 1, this shows an embodiment of implantable medical device 10 deployed in the vena cava 12 of a patient. The medical device has a longitudinal dimension extending to first and second ends 14 and 16. The medical device 10 includes a material capture element 18 which has a generally closed conical deployed shape with a narrow end 20 disposed at or proximate the first end 14 of the device 10, and a wide end 22 facing the second end 16 of the device 10.

The material capture element 18 in this embodiment is configured as a filter and is formed of a plurality of wires 24 arranged in the form of a cone having a narrow end in which the wires 24 pass into a metal bushing 26, in the form of a sleeve or cup. At the end of the bushing 26 there is provided a hook 28. The wires 24 may be welded, bonded or a friction fit, for example, to the inside of the lumen of the bushing 26 and the hook 28 may be likewise welded, bonded or otherwise formed as a part of the bushing 26. The wires 24 extend to the wide end 22 of the material capture element 18. It will be apparent to the skilled person that the wires 24 are preferably circumferentially equally spaced from one another. In the example shown in FIG. 1, there are provided eight wires 24 but their number will be dependent upon the deployed size of the device 10, the diameter of the wires 24 and the degree of filtering desired. The wires 24 preferably have a curved shape and are of a number which allows for minimum trauma to the vessel as the radial forces are distributed at several points.

The bushing 26 is provided in this embodiment but is not essential as the wires could be coupled together is a different manner, for example by welding, by being cut forma common rod or cannula and so on.

As can be seen in FIG. 1, extending from and attached to the wires 24 are wire sections 30 which extend in curved manner so as to close the gap between the wires 24 towards the wider end 22 of the material capture element 18. In the example shown in FIG. 1, there are provided two wire sections 30 to each wire 24 and these extend in opposing directions in what could be described as a leaf shape. The wire sections 30 may be welded or otherwise bonded at their ends to their associated wire 24. In other embodiments they could be cut from a common metal blank. In other embodiments, the wire sections 30 may simply be wrapped or coiled around the associated wires 24. Elements 36 and 38 depict the connection points of the wires 30 to the wires 24 and of the wires 40 to the wires 24, respectively.

This shape of wires 24 and wire sections 30 creates apertures within the material capture element 18 which allow for the passage of fluid therethrough but which are small enough to trap particulate material, such as plaque, thrombus material and the like, within the material capture element 18. The skilled person will be aware of the optimum size of the apertures of such a filter and thus of the sizes, number of wires 24 and 30 and their distribution at the conical periphery of the material capture element 18. This structure is preferred in contrast to a filter having a frame and covering mesh as it has a smaller volume allowing it to be compressed radially to a smaller diameter, although it is not excluded that the material capture element 18 could be formed as a frame and covering mesh.

The wires 24 of the material capture element 18 open radially from the first end 14 towards the wide end 22 in a generally linear manner, although in this embodiment curve slightly inwardly at the wide end 22, in a manner to create a first series of contact points 32 at the positions of maximum radius of the wires 24. The reader will appreciate that the wires 24 will create a plurality of contact points 32 arranged and spaced circumferentially around the wide end of the cone of the material capture element 18, these contact points 32 providing a first contact site of the device 10.

The wire sections 30 are preferably disposed along the periphery of the cone of the material capture element 18 and thus define with the wires 24 the shape of the material capture element 18.

The wires 24 and wire sections 30 may be formed from distinct wires of round cross-section but in other embodiments may be cut from a common blank, for example from a cannula or cone. Cutting can usefully be by laser.

The configuration of wires 24 and wire sections 30 as shown in the Figures provides a structure which is able to be compressed radially to a small diameter, useful for endoluminal delivery through a small diameter introducer assembly. This enables the device 10 to be delivered even through narrow and/or tortuous vessels.

Either or both of the connection points 36, 38 could in some embodiments also be annular or other shaped supports for supporting one or more sets of radiopaque markers for locating the device 10 in a patient's vessel. A first set of radiopaque markers could be located at the junction 36 of the wire sections 30 to their respective wires 24 adjacent the wide end 22 of the material capture element 18. The second set of radiopaque markers could be located at the junction 38 of the wires 24 with respective wire tethers 40. It will be appreciated that only one set of radiopaque markers may be provided.

Such radiopaque markers would typically be of gold or other radiopaque material and may be held within annular recesses or openings at the junctions 36, 38 in a manner known in the art.

The wire tethers 40 extend to the second end 16 of the device 10 and in particular to a second bushing 42 which in this embodiment has the same characteristics as the bushing 26 and is equally provided with a hook 44. The second hook 44 faces the opposite direction relative to the first hook 28.

As with the wires 24, the wire tethers 40 are circumferentially spaced around the circumference of the device 10. In the example shown in FIG. 1, there are provided eight wire tethers 40, although this number may be different. It is not necessary to have the same number of wire tethers 40 as wires 24, although having the same number provides a convenient structure. As will be apparent in particular from the uppermost and lowermost wire tethers 40 visible in FIG. 1, these have a curving shape in which they curve radially inwardly from their junction with the wires 24, or radiopaque markers 38, towards a point of minimum radius or waist 46 and then outwardly again towards a point of maximum radius 50, before tapering in substantially linear manner towards the second bushing 42 to form a generally conical end portion 52 to the wire tethers 40.

As can be seen particularly in FIG. 1, the points of maximum radius 50 abut the vessel wall 12 at a second contact site longitudinally spaced from the first contact site 32. These two spaced contact sites 32, 50 ensure that the device 10 remains properly aligned in the vessel 12 with no risk of tilting, particularly of the material capture element 18. This positioning also ensures that the wide end 22 of the material capture element 18 is maintained aligned with the normal to the vessel, that is with a plane perpendicular to the centreline of the vessel 12.

The wire tethers 40 have a generally open structure which provides a substantially open passageway for blood and particulate material therethrough. As a result, there is no impediment or disturbance to the flow of blood through the structure of the wire tethers 40. This will minimize the creation of stagnant blood at the wire tethers and will minimize blood clotting in this zone of the device 10. All significant blood disturbances occur at and within the material capture element 18 and thus any clotting will be confined to this part of the device 10.

The wires 24, 30 and 40 are advantageously made from metal alloys, including for example nickel titanium alloy such as Nitinol, cobalt chromium or any other alloys with good fatigue properties and good elastic performance. In other embodiments, the wires could be formed of a spring material such as spring steel. Parts of the filter could be made of or include a biodegradable material, such as magnesium or a plastic polymer for example. The person skilled in the art will be aware of suitable materials.

Figure 2:
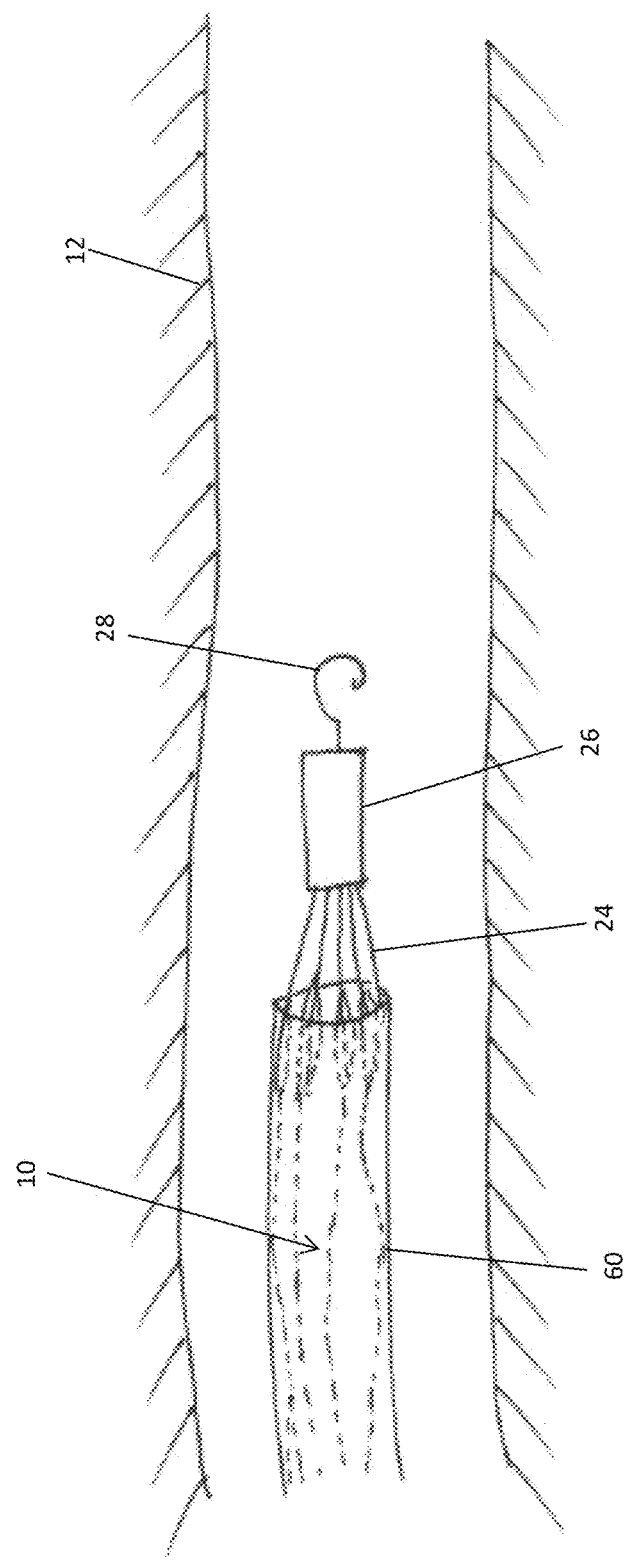
FIG. 2 shows the filter of FIG. 1 in the process of being deployed from an introducer assembly.

In addition to improving the stability of the medical device 10 in a patient, the structure is double-ended, which enables deployment, repositioning and retrieval from both directions, as the device 10 can be deployed as well as collapsed and repositioned or withdrawn from the vessel from either end. Referring to FIG. 2, this shows in schematic form only the deployment of the device 10 into the vena cava 12 of a patient. This would typically be achieved by an introducer assembly of generally conventional form, in which the device 10 is held within a sheath 60. The introducer assembly will comprise a variety of components including, for example, pusher elements, constraining wires and the like for holding the medical device 10 radially constrained within the introducer assembly until it is to be deployed within a patient, as will be apparent to the person skilled in the art.

The device 10 is typically deployed from the end 14 first, such that the material capture element 18 is expanded first from the introducer assembly. The device 10 is progressively released from the sheath 60, all the way to its second end 16. Once deployed from the introducer assembly, it is still possible to reposition the medical device 10, for example by pulling from either end of the device 10 by means of the respective hook 28, 44. It will be appreciated that in pulling the medical device 10, this will draw the wire elements of the device 10 radially inwardly effectively reducing its diameter, thereby assisting moving the device within the vessel. The device 10 can be pulled in either direction so as to achieve accurate positioning within the vessel 12.

Figure 3:
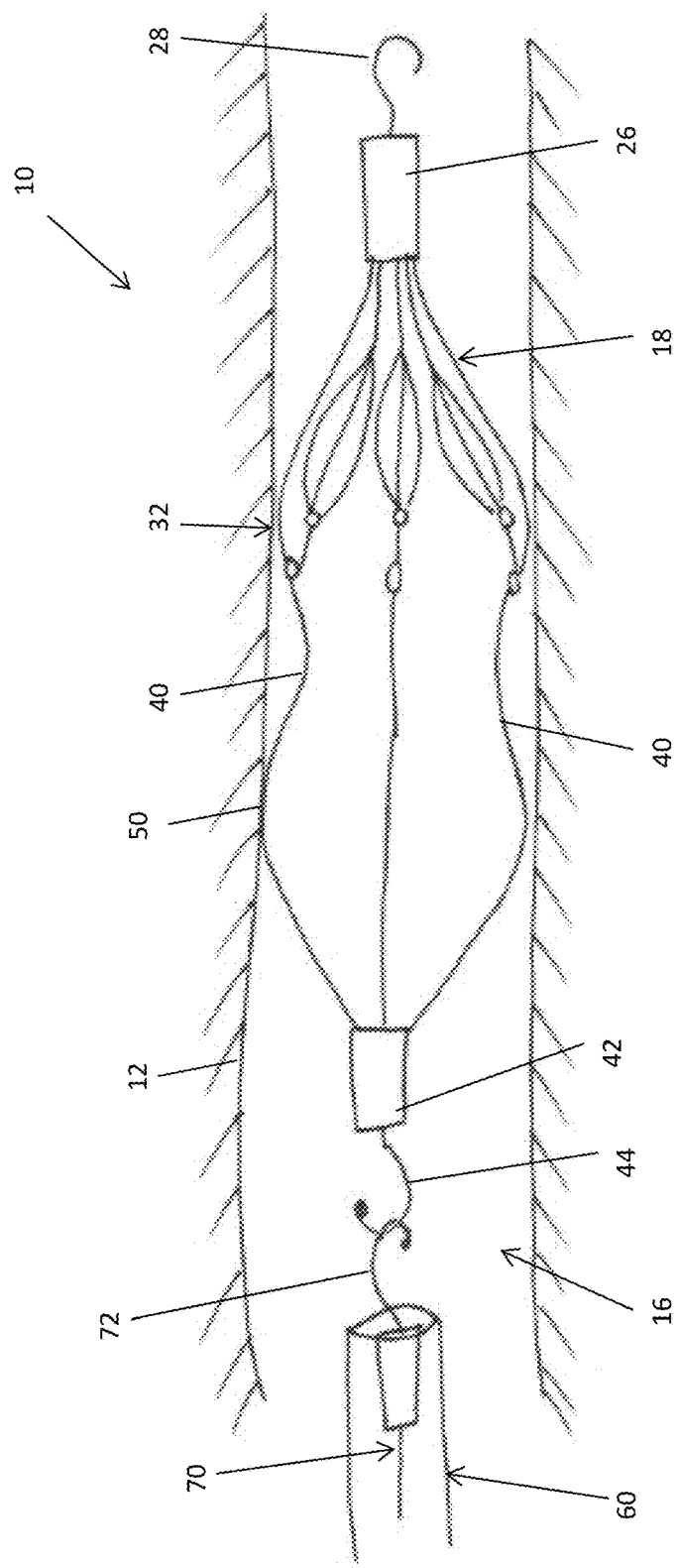
FIG. 3 shows the filter of FIG. 1 in the process of being retrieved from the vena cava of a patient.

Similarly, the device 10 can be removed from a patient's vessel from either end and in this regard in FIG. 3 there is shown a removal assembly which includes a sheath 60 and a removal device 70 which includes a hook 72 able to hook onto, in this example, the second hook 44 of the medical device 10. By retracting the retrieval device 70 within the sheath 60, the medical device 10 will be progressively pulled into the sheath 60, with in this example the wire tethers 40 eventually being radially compressed into the sheath 60. The radial compression of the wire tethers 40 will also compress radially the material capture element 18 so that the entire medical device 10 can be entirely drawn into the sheath 60.

The provision of double hooks 28, 44 also enables the medical device 10 to be drawn into a retrieval sheath 60 from the end 14 of the device 10, that is from the material capture element 10 first.

It is to be appreciated that one or more of the hooks 28, 44, 72 could be replaced by another form of grasping element, or the ends of the device 10 could potentially just be welded to a deployment/retrieval device as an alternative.

The embodiments described above form the filtration structure by means of an arrangement of wires 24, 30. Other embodiments can provide a filtration structure formed of a mesh of material which is held to a wire frame, in which case the wire structure of the filtration element 18 can have a similar structure to that of the wire tethers 44. Similarly, although the embodiments described above relate to a filter assembly, the structure can also be used as an occlusion device, in which case the material capture element 18, instead of filtering would occlude. This could be achieved, for example, by providing the structure 18 as a sheet of impermeable material or by covering a frame with an impermeable material, such as an impermeable fabric.

In other embodiments, the material capture element 18 could have a different structure, for example, a braided structure or the like.

The wires 24, 30, 44 could be made of shape memory materials or spring materials.

It will be appreciated also that the wire elements 20, 26 and 32 could be laser cut from a cannula.

In some embodiments there may be provided barbs or other anchor elements, typically extending from the wires 24, 40, for enhancing the fixation of the device 10 in the vessel 12. Such anchors or barbs could usefully be located at either or both of the contact positions 32 and 50 and extending from the wires 24 and 40.

A typical dimension for vena cava filter would be a diameter of around 30 mm when radially expanded and a length of around 50 mm.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. An implantable medical device having a first end, a second end, and a longitudinal dimension, the device including:
    a material capture element comprising a plurality of first wires extending from the first end to define a generally closed conical deployed shape with a narrow end disposed at or proximate the first end of the device, and a wide end facing the second end of the device, the material capture element having a zone of wider radial dimension providing a first vessel contact site of the device, the material capture element comprising a plurality of second wires, each second wire being fixedly attached to a first wire at a first connection point and a second connection point to define two second wire segments attached to each first wire in circumferentially opposing directions to define a plurality of apertures, the first connection point and the second connection point being spaced apart from the first end and the second end;
    a plurality of wire tethers each coupled to the material capture element at a plurality of junctions at the wide end thereof, the wire tethers extending to the second end of the device and defining a substantially open passageway for blood and particulate material therethrough, the wire tethers having portions of wider radial dimension providing a second vessel contact site of the device, the first and second contact sites being spaced from one another along the longitudinal dimension of the device;
    a first retrieval element disposed at the first end of the device and coupled to the narrow end of the material capture element; and
    a second retrieval element disposed at the second end of the device and coupled to the wire tethers.

2. The device according to claim 1 wherein the material capture element provides a substantially closed conical capture basket.

3. The device according to claim 1 wherein the wire tethers have a curved deployed shape providing said portions of wider radial dimension.

4. The device according to claim 1 wherein the wide end of the material capture element has a taper, said taper providing the zone of wider radial dimension and first vessel contact site.

5. The device according to claim 1 wherein the first and second contact sites each include circumferentially spaced contact elements.

6. The device according to claim 1 including more than two contact sites along the length of the device, the contact sites being spaced from one another.

7. The device according to claim 1 wherein the wire tethers taper to the second end of the device.

8. The device according to claim 1 wherein the first and second retrieval elements face opposing directions.

9. The device according to claim 1 wherein the first and second retrieval elements include a retrieval hook.

10. The device according to claim 1 wherein the device is a filter.

11. A method of deploying an implantable medical device, the device having a first end and a second end and including:
    a material capture element comprising a plurality of first wires extending from the first end to define a generally closed conical deployed shape with a narrow end disposed at or proximate the first end of the device, and a wide end facing the second end of the device, the material capture element having a zone of wider radial dimension providing a first vessel contact site of the device, the material capture element comprising a plurality of second wires, each second wire being fixedly attached to a first wire at a first connection point and a second connection point to define two second wire segments attached to each first wire in circumferentially opposing directions to define a plurality of apertures, the first connection point and the second connection point being spaced apart from the first end and the second end;
    a plurality of wire tethers each coupled to the material capture element at a plurality of junctions at the wide end thereof, the wire tethers extending to the second end of the device and defining a substantially open passageway for blood and particulate material therethrough, the wire tethers having portions of wider radial dimension providing a second vessel contact site of the device, the first and second contact sites being spaced from one another along the longitudinal dimension of the device;

a first retrieval element disposed at the first end of the device and coupled to the narrow end of the material capture element; and a second retrieval element disposed at the second end of the device and coupled to the wire tethers; the method including the steps of:

inserting the device endoluminally in a patient in a radially contracted configuration;

providing for expansion of the device in a vessel of the patient with the first end of the device in a downstream blood flow position relative to the second end of the device such that the material capture element is disposed with the open end thereof facing upstream; whereby the first and second contact sites maintain orientation of the device in the vessel.

12. The method of claim 11 further comprising:

subsequently retrieving the medical device from the patient by coupling a retrieval apparatus to the second retrieval element from an upstream direction of the vessel, the retrieval apparatus including a sheath sized to receive the medical device, the wire tethers acting to pull and radially compress the material capture element into the sheath.

13. The device of claim 1, wherein at least one first connection point comprises a support for a radiopaque marker.

14. The device of claim 13, wherein the support comprises an annular member.

15. The device of claim 1, wherein at least one second connection point comprises a support for a radiopaque marker.

16. The device of claim 15, wherein the support comprises an annular member.

17. The device of claim 1, wherein at least one junction comprises a support for a radiopaque marker.

18. The device of claim 17, wherein the support comprises an annular member.

* * * * *